Figure 1:
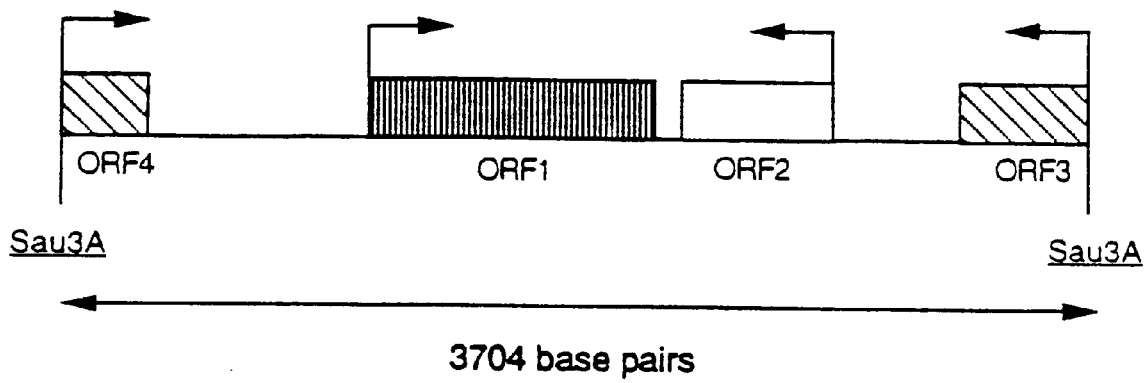

United States Patent [19]
Prevots et al.

[11] Patent Number: 5,955,332
[45] Date of Patent: Sep. 21, 1999

[54] NUCLEIC ACID SEQUENCES AND PLASMIDS COMPRISING AT LEAST ONE PHAGE RESISTANCE MECHANISM, BACTERIA CONTAINING THEM AND THEIR USE

[75] Inventors: Fabien Prevots, Toulouse; Sandrine Tolou; Marlène Daloyau, both of Castanet, all of France

[73] Assignee: Systems Bio-Industries, Boulogne, France

[21] Appl. No.: 08/702,153

[22] Filed: Aug. 23, 1996

[51] Int. Cl.$^6$ .............................. C12N 15/03; C12N 1/21; C07H 21/04
[52] U.S. Cl. .................................... 435/172.3; 435/252.3; 435/320.1; 536/23.7
[58] Field of Search .............................. 435/252.3, 320.1, 435/172.3; 536/23.7

[56] References Cited

U.S. PATENT DOCUMENTS 4,883,756  11/1989  Klaenhammer et al. ............. 435/252.3

FOREIGN PATENT DOCUMENTS

| | | |
|---|---|---|
| 0208468A3 | 1/1987 | European Pat. Off. . |
| 0246909A2 | 11/1987 | European Pat. Off. . |
| 0355036A1 | 2/1990 | European Pat. Off. . |
| 0452224A1 | 10/1991 | European Pat. Off. . |
| WO92/05260 | 4/1992 | WIPO . |

OTHER PUBLICATIONS

Jarvis et al. Applied and Environmental Microbiology 55(6): 1537–1543 (1989).
Hill et al. Applied and Environmental Microbiology 55(7): 1684–1689 (1989).
Steenson et al. Applied and Environmental Microbiology 50(4): 851–858 (1985).
Steele et al. Plasmid 22: 32–43 (1989).
Laible et al. J. Diary Science 70: 2211–2219 (1987).
Froseth et al. J. Diary Science 71: 275–284 (1988).
Sanders et al. Applied and Environmental Microbiology 47(5): 979–985 (1984).
Sanders. Biochimie 70: 411–421 (1988).
Gautier et al. Applied and Environmental Microbiology 53(5): 923–927 (1987).
Josephsen et al. Plasmid 23: 71–75 (1990).
Klaenhammer et al. Journal of General Microbiology 131: 1531–1541 (1985).
Coffey et al. Neth. Milk Dairy J. 43: 229–244 (1989).
Vlegels et al. Neth. Milk Dairy J. 43: 245–259 (1989).
Sanders et al. Applied and Environmental Microbiology 46(5): 1125–1133 (1983).
Jarvis et al. Applied and Environmental Microbiology 54: 777–783 (1988).
Hill et al. Applied and Environmental Microbiology 56(7): 2255–2258 (1990).
Prevots et al. Applied and Environmental Microbiology 56(7): 2180–2185 (1990).
Lerayer. Revista de Microbiologia 20(2): 197–209 (1989).
Klaenhammer. J. Diary Science 72: 3429–3443.

*Primary Examiner*—James Ketter
*Assistant Examiner*—John S. Brusca
*Attorney, Agent, or Firm*—Foley & Lardner

[57] ABSTRACT

The invention relates to polynucleotides of 1345 bp and 3704 bp and the like, which comprise at least one phage resistance mechanism and obtainable from the total DNA contained in the *Lactococcus lactis* ssp *cremoris* strain deposited in the CNCM under No. I-941.

13 Claims, 2 Drawing Sheets

Organization of the ORF
deduced from the sequence of the fragment of 3704 base pairs
derived from the strain S94, cloned into plasmid pLDP1
and conferring phage resistance.

ORF1: open reading frame of 1038 bp
ORF2: open reading frame of 573 bp

ORF3
           2 truncated open reading frames
ORF4

⟶   direction of gene transcription

Amplification of 2 internal fragments
of the fragment of 3704 base pairs by PCR

NUCLEIC ACID SEQUENCES AND PLASMIDS COMPRISING AT LEAST ONE PHAGE RESISTANCE MECHANISM, BACTERIA CONTAINING THEM AND THEIR USE

The present invention relates to novel nucleic acid sequences and plasmids capable of hybridizing therewith and carrying at least one phage resistance mechanism, to the lactic acid bacteria containing these sequences or these plasmids, in particular the lactococci belonging to the species *Lactococcus lactis,* to the use of certain strains of these lactococci for transferring a phage resistance mechanism, especially by conjugation, to strains of industrial interest, particularly in the dairy industry, and to the use of certain strains of *Lactococcus lactis* for obtaining these plasmids.

Lactic acid bacteria are involved in the production and preservation of a large number of foodstuffs such as cheeses, butter, yogurts, sausage or sauerkraut. Among these, dairy products occupy a particularly important position. The industrial conversion of milk is carried out in ever larger fermentation vats, in which the appearance of phages of lactic acid bacteria can have serious or even catastrophic consequences, namely a variation in the characteristics, especially organoleptic characteristics, of the final product, a loss of product present in the vat, and the need to decontaminate the latter as well as the surrounding installations. The dairy industry is therefore in urgent need of novel means and novel methods of rendering bacteria more resistant to phages.

The phages of lactic acid bacteria belong to three major homology groups (I), (II) and (III) defined by DNA/DNA hybridization studies according to RELANO P. et al., (1987), J. Gen. Microbiol. 133, 3053–3063. Groups (I) and (III) comprise only virulent phages. Group (II) comprises virulent phages and temperate phages. The homologies are strong within one and the same group and very weak between groups. The phages of group (I) have an oblong nucleocapsid while the phages of groups (II) and (III) have an isometric nucleocapsid.

Several natural phage resistance mechanisms are known to exist, the three main ones being:

inhibition of phage adsorption; in this mechanism, the adsorption of the phage by the bacterium is inhibited or delayed.

the restriction/modification system; this system involves a restriction enzyme, which degrades the DNA of the phage as soon as it enters the bacterium.

abortive infection; according to this third mechanism, phage adsorption is normal but phage multiplication does not take place.

These mechanisms are described in detail by SANDERS M. in Biochimie 70, (1988), 411–421.

The development of phage resistant lactic acid bacteria has already been the subject of numerous studies.

In this connection, reference may be made to the following articles in particular:

VLEGELS et al.; Neth. Milk and Dairy J. 43, (1989), 245–259;

SANDERS and KLAENHAMMER; Applied and Environ. Microbiol. (1983), vol. 46, 1125–1133;

these articles relate to plasmids which inhibit phage adsorption;

Audrey W. JARVIS; Applied and Environ. Microbiol.; March 1988, p. 777–783;

EP-A3-0 208 468;

COFFEY et al.; Neth. Milk and Dairy J. 43, (1989), 229–244;

KLAENHAMMER and SANOZKY; Journal of General Microbiology (1985), 131, 1531–1541;

DURMAZ et al.; J. Bacteriol. (1992), 7463–7469;

these articles describe plasmids which confer phage resistance by the abortive infection mechanism;

JOSEPHSEN and KLAENHAMMER, Plasmid 23, 71–75, (1990);

MOINEAU et al.; Applied and Environ. Microbiol. (1995), 2193–2202;

U.S. Pat. No. 4,883,756;

GAUTIER and CHOPIN; Applied and Environ. Microbiol. (1987), 53, p. 923–927;

McLANDSBOROUGH et al.; Applied and Environ. Microbiol. (1995), 2023–2026;

these last articles describe especially plasmids which confer phage resistance by the restriction/modification mechanism.

Patent application EP-A1-452 224 also describes a DNA sequence comprising at least one phage resistance mechanism; this DNA sequence contains a functional portion of the HindIII—HindIII fragment of about 3.3 kb of plasmid pPF144-1 present in the *Escherichia coli* strain deposited on Apr. 9, 1991 in the CNCM (Collection Nationale de Cultures de Microorganismes, Institut Pasteur, Paris, France) under no. I-1070.

This HindIII—HindIII fragment of about 3.3 kb was isolated from plasmid pPF144 contained in the *Lactococcus lactis* ssp *lactis* strain deposited in the CNCM on Apr. 12, 1990 under no. I-945, which is a transconjugant resulting from the crossing of the donor strain *Lactococcus lactis* ssp *lactis* S91, deposited in the CNCM on Apr. 12, 1990 under no. I-940, and the recipient strain *Lactococcus lactis* ssp *lactis* S45, derived from the strain *Lactococcus lactis* ssp *lactis* C2-LL described by McKay et al., 1977, in J. Bacteriol. 257–265. This fragment carries one or more phage resistance mechanisms.

Following this work, a DNA sequence of 1.9 kb which by itself confers phage resistance was isolated from this HindIII—HindIII DNA sequence of 3.3 kb. This novel DNA sequence of about 1.9 kb was described in EP-A1-643 134.

The Applicant has isolated a fragment of 3704 base pairs (bp) from the total DNA of the strain *Lactococcus lactis* ssp *diacetylactis* S94, deposited in the CNCM on Apr. 12, 1990 under no. I-941, by partial digestion with the restriction enzyme Sau3A.

This fragment carries one or more phage resistance mechanisms and by itself confers phage resistance.

From this DNA sequence of 3704 bp, the Applicant subsequently isolated a DNA sequence of 1345 bp which by itself confers phage resistance.

The present invention therefore relates to two novel DNA sequences comprising at least one phage resistance mechanism, said sequences respectively containing 3704 bp and 1345 bp and consisting of:

a) the DNA sequences having the nucleic acid series of [SEQ ID No 1] or [SEQ ID No 3];

b) the DNA sequences hybridizing with the above sequences or a fragment thereof; and c) the corresponding mRNA and cDNA sequences.

The sequences [SEQ ID No. 2] and [SEQ ID No. 4] are the amino acid sequences deduced from the sequences [SEQ ID No. 1] and [SEQ ID No. 3] respectively.

The sequence [SEQ ID No. 3] is a DNA fragment of 1345 bp contained within the sequence [SEQ ID No. 1].

This fragment of 1345 bp can be obtained by the PCR method using the following two oligonucleotides:

oligonucleotide no. 1 [SEQ No. 5]:

```
oligonucleotide no. 1 [SEQ No. 5]:

5' TCATAGGATCCAATAATCAACTAGCAATTCG 3'
              BamHI oligonucleotide no. 2 [SEQ No. 6]:

5' CATTAGTCGACAAATACAGGCTCTATAAAGC 3'
              SalI
```

The invention particularly relates to the DNA sequences respectively containing:

3704 bp and having the nucleic acid sequence [SEQ ID No. 1] below; and 1345 bp and having the nucleic acid sequence [SEQ ID No. 3] below.

The invention further relates to the DNA sequences which have a high degree of homology with the DNA sequences [SEQ ID No. 1] and [SEQ ID No. 3] above. A high degree of homology means a homology (ratio of the identical nucleotides to the total number of nucleotides) of at least 70%, preferably at least 80%, of the nucleotide sequences when they are aligned according to the maximum homology by the optimal sequence alignment method of Needleman and Wunsch, 1970, J. Mol. Biol. 48, 443–453. This method is used especially in the UWGCG software of the University of Wisconsin: Devereux et al., 1984, Nucl. Ac. Res. 12, 8711–8721—option GAP.

The present invention particularly relates to the DNA sequences which hybridize with the DNA sequence [SEQ ID No 1] and [SEQ ID No 3] or a fragment thereof. In the present specification the term "hybridization" designated the conventional hybridization conditions and more particularly the stringent hybridization conditions.

The invention further relates to the plasmids transformed with one of the nucleic acid sequences according to the invention. A possible example of these plasmids is plasmid pLDP1 into which one of the DNA sequences according to the invention has been cloned by the customary techniques known to those skilled in the art. Plasmid pLDP1 is derived from plasmid pVA838 (Macrina F. L. et al., Gene 19, 345–353) by deletion of the 1523 bp fragment between the HindIII site (0) and the EcoRI site (1523) and replacement thereof with 54 base pairs corresponding to the multiple cloning sites of plasmid pUC18 (Yanisch-Perron C. et al.; 1985—Gene 33, 103—119) which are flanked by the EcoRI and HindIII sites.

The invention further relates to the phage resistant lactic acid bacteria, preferably belonging to the species *Lactococcus lactis,* which contain at least one of the nucleic acid sequences or one plasmid as defined above.

These nucleic acid sequences or these plasmids may have been introduced into the lactic acid bacteria by conjugation, transformation, protoplast fusion or any other gene transfer method well known to those skilled in the art.

The lactic acid bacteria which can advantageously be transformed with the DNA sequences according to the invention, or a plasmid containing them, are for example the strains of *Lactococcus lactis* ssp *cremoris, Lactococcus lactis* ssp *lactis* and *Lactococcus lactis* ssp *lactis* var. *diacetylactis.*

These strains transformed in this way can be used for transmitting a phage resistance mechanism to a strain of industrial interest by conjugation, transformation, transduction, protoplast fusion or any other gene transfer method well known to those skilled in the art. This mechanism can be carried by a plasmid or by another part of the bacterial genome. If it is carried by a plasmid, it is advantageously transferred by conjugation.

The invention further relates to the phage resistant strains of industrial interest obtained in this way.

The invention will be understood more clearly with the aid of the following Examples, which comprise experimental results and a discussion thereof. Some of these Examples relate to experiments performed for the purpose of carrying out the invention; others relate to embodiments of the invention, which are of course given purely by way of illustration.

The majority of the techniques described in these Examples, which are well known to those skilled in the art, are explained in detail in the work by Sambrook, Fritsch and Maniatis entitled "Molecular cloning; a Laboratory Manual", published in 1989 by Cold Spring Harbor Press, New York (2nd edition).

The following description will be understood more clearly with the aid of FIGS. 1 and 2 below, which respectively show:

FIG. 1: Organization of the ORF deduced from the sequence of the fragment of 3704 base pairs.

Figure 2:
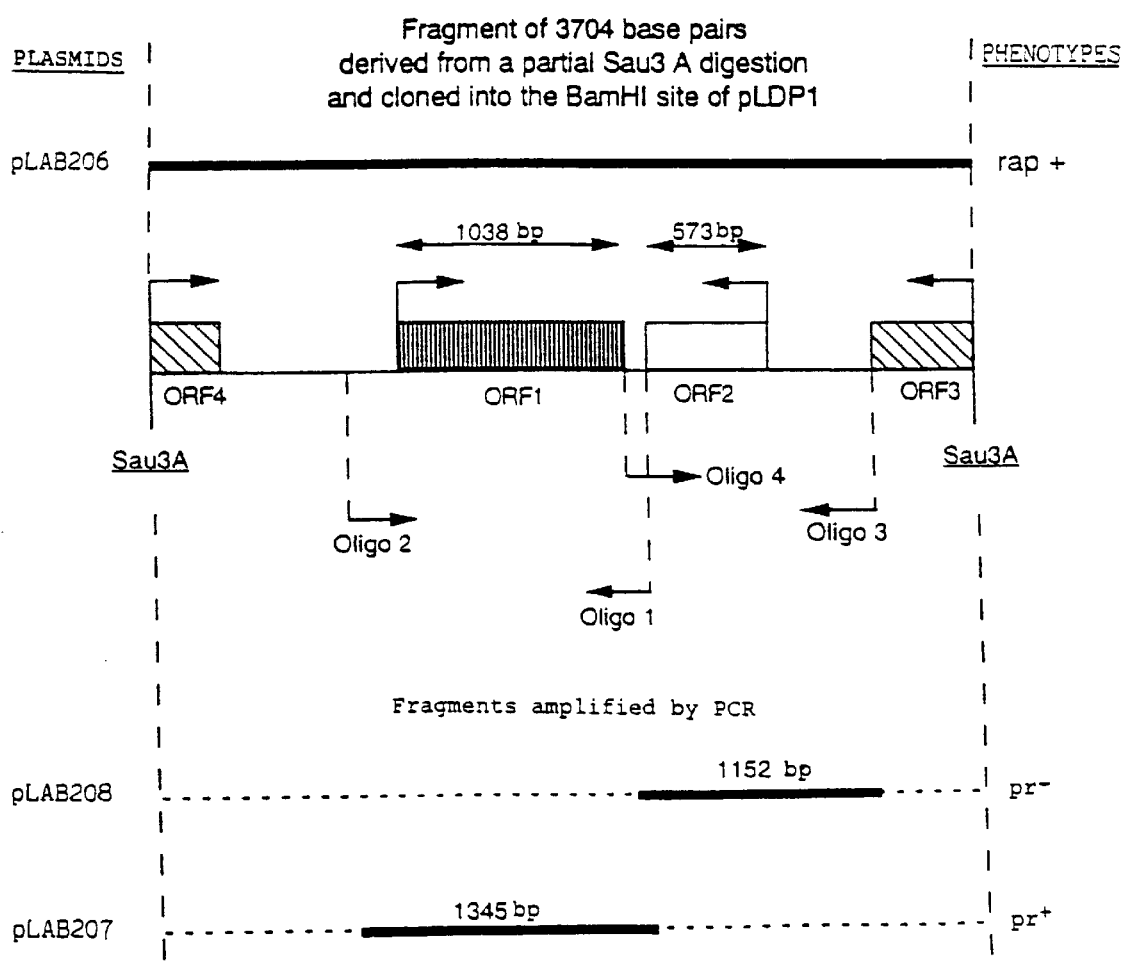

FIG. 2: Amplification, by PCR, of 2 internal fragments of the fragment of 3704 bp conferring phage resistance.

EXAMPLE 1

Sequence of the Fragment of 3704 bp

The strain *Lactococcus lactis* ssp *diacetylactis* S94, deposited in the CNCM on Apr. 13, 1990 under no. I-941, contains one or more phage resistance mechanisms. In particular, it has transferred plasmid pPF72 by conjugation into the recipient strain *Lactococcus lactis* S45, derived from the strain *Lactococcus lactis* C2-LL described by McKay et al., 1977, J. Bacteriol. 257–265, said plasmid conferring resistance to phages Ø 53 (group I) and Ø 59 (group III). Other phage resistance mechanisms may be present in the strain I-941. It is for this reason that a total DNA library was constructed from the strain I-941. The restriction fragment of 3704 bp conferring phage resistance, obtained by a partial digestion of the total DNA of the strain S94 (I-941) with the restriction enzyme Sau3A, was cloned into vector pLDP1 at the BamHI site. The recombinant plasmid pLAB206 obtained confers a total resistance to phage Ø 59 to the strain *Lactococcus lactis* ssp *lactis* MG 1363 disclosed by GASSON M. J. (1983) in J. Bacteriol. 154: 1–9, hereinafter named strain *L. lactis* S56 or S56.

The nucleic acid sequence of this fragment of 3704 bp, determined by the method of Sanger et al. (PNAS—USA, 14, 5463, 1977), is the sequence [SEQ ID No. 1] below.

Analysis of the sequence showed that the fragment of 3704 bp possesses 2 complete open reading frames (ORF1 and ORF2) and two truncated open reading frames (ORF3 and ORF4) containing only the N-terminal parts (FIG. 1).

EXAMPLE 2

Amplification of an Internal Fragment of the 3704 bp Fragment by PCR

The PCR (Polymerase Chain Reaction) technique, described for example in the work by Maniatis cited above, makes it possible to amplify a DNA fragment contained between two appropriately chosen oligonucleotides. This amplified DNA can easily be cloned if restriction sites are provided by the oligonucleotides. In fact, the sequences of these oligonucleotides can contain, at their 5' end, a heterologous part of the DNA to be amplified, consisting of 10 to 12 base pairs, for example, 6 of which constitute a restriction site.

This technique was applied in order to determine whether one or other of the two open reading frames (ORF1, ORF2) identified in the nucleotide sequence of the 3704 bp fragment corresponds to a phage resistance gene, but also in order to form a probe specific to this gene.

This was done by synthesizing 4 oligonucleotides of 31 and 32 bases (6 of which constitute a restriction site).

These 4 oligonucleotides have the following sequences: oligonucleotide no. 1 [SEQ No.5]:

oligonucleotide no. 1 [SEQ No. 5]:

5' TCATA<u>GGATCC</u>AATAATCAACTAGCAATTCG 3'
          <u>BamHI</u> oligonucleotide no. 2 [SEQ No. 6]:

5' CATTA<u>GTCGAC</u>AAATACAGGCTCTATAAAGC 3'
          <u>SalI</u> oligonucleotide no. 3 [SEQ No. 7]:

5' TCATA<u>GGATCC</u>TTAACAATAAAATTACTCTGC 3'
          <u>BamHI</u> oligonucleotide no. 4 [SEQ No. 8]:

5' CATTA<u>GTCGAC</u>TTAAATTTGATATTGATTGCG 3'
          <u>SalI</u>

Their locations on the 3704 bp fragment are indicated in FIG. 2.

The oligonucleotides no. 1 and 2 made it possible to amplify a DNA fragment of 1345 bp containing ORF1 of 1038 bp in the form of a BamHI-SalI fragment, by virtue of the restriction sites provided by the oligonucleotides, enabling directional cloning into shuttle plasmid pLDP1.

Likewise, the oligonucleotides no. 3 and 4 made it possible to amplify a DNA fragment of 1152 bp containing ORF2 of 573 bp in the form of a BamHI-SalI fragment, as above.

The DNA fragments were amplified by PCR, starting from a total DNA preparation of the strain S94 (I-941), with conventional Taq polymerase.

The PCR products were purified by phenol/chloroform extraction, precipitated with ethanol, digested with the restriction enzymes BamHI and SalI and cloned into shuttle vector pLDP1 open at the BamHI and SalI sites.

Cloning of these fragments into vector pLDP1 produced recombinant plasmids pLAB207 and pLAB 208. These plasmids were introduced into the strain *E. coli* TG1 and into the strain *L. lactis* S56.

The introduction of plasmids pLAB207 and pLAB 208 into the strain *L. lactis* S56 made it possible to determine whether they confer phage resistance.

The results pertaining to the cloning of the various amplified DNA fragments are summarized in Table 1 below:

TABLE 1

| Pair of oligo-nucleotides | Size of the fragment | Sites added | Cloned into pLDP1 | Phenotype* |
|---|---|---|---|---|
| 1–2 | 1345 bp | BamHI—SalI | pLAB207 | pr+ |
| 3–4 | 1152 bp | BamHI—SalI | pLAB208 | pr− |

*phenotypes:
pr+ = phage resistance
pr− = no phage resistance

EXAMPLE 3

Phage Resistance Conferred by Plasmid pLAB207

Plasmid pLAB207 was introduced into the strain *L. lactis* S56.

The phage resistance of the clones obtained was tested by performing a titration (PFU/ml) with phages Ø 53 and Ø 59.

The results are given below:

| | Phage Ø 53 (I) | | Phage Ø 59 (III) | |
|---|---|---|---|---|
| Strain | Titer (PFU/ml) | Size of the plaques (mm) | Titer (PFU/ml) | Size of the plaques (mm) |
| S56 | $10^{10}$ | 3 | $3 \cdot 10^9$ | 2 |
| S56 (pLDP1) | $6 \times 10^9$ | 3 | $2 \times 10^9$ | 2 |
| S56 (pLAB207) | $10^6$ | 0.5 | 0 | — |

PFU/ml = plate forming units per ml

Plasmid pLAB207 containing the PCR-amplified fragment of 1345 bp corresponding to ORF1 confers phage resistance.

---

What is claimed is:

1. A polynucleotide comprising at least one phage resistance mechanism, said polynucleotide selected from the group consisting of:

(a) a DNA having the nucleic acid sequence of SEQ ID NO. 1 or SEQ ID NO. 3;

(b) a DNA having at least 70% homology with (a); and (c) the corresponding mRNA and cDNA polynucleotide of (a) or (b).

2. A polynucleotide according to claim 1, wherein the polynucleotide has a sequence according to sequences SEQ ID No. 1 and SEQ ID No. 3 or is at least 70% homologous with said sequences.

3. A plasmid comprising at least one phage resistance mechanism and containing a polynucleotide according to claim 1.

4. A plasmid comprising at least one phage resistance mechanism and containing a polynucleotide according to claim 2.

5. A phage resistant lactic acid bacterium which contains at least one plasmid according to claim 2.

6. A phage resistant lactic acid bacterium which contains at least one plasmid according to claim 3.

7. A method of conferring phage resistance to a bacterium, comprising
   introducing a plasmid according to claim 3 into the bacterium.

8. A method of conferring phage resistance to a bacterium, comprising
   introducing a plasmid according to claim 4 into the bacterium.

9. A polynucleotide according to claim 1, wherein the DNA of (b) has at least 80% homology with (a).

10. A polynucleotide according to claim 2, wherein the degree of homology is at least 80%.

11. A polynucleotide encoding a polypeptide that confers phage resistance to a bacterium, wherein the polypeptide has the sequence of SEQ ID NO:2 or SEQ ID NO:4.

12. A polynucleotide according to claim 11, wherein the polynucleotide has the sequence of SEQ ID NO:1 or SEQ ID NO:3.

13. A polynucleotide comprising at least one phage resistant mechanism, wherein the polynucleotide is selected from the sequences SEQ ID NO. 1 and SEQ ID NO. 3 or a sequence which has a high degree of homology with said sequences SEQ ID NO. 1 and SEQ ID NO. 3.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 3704 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
    (A) ORGANISM: Lactococcus lactis (ix) FEATURE:
    (A) NAME/KEY: CDS
    (B) LOCATION:1095..2132

(xi) SEQUENCE DESCRIPTION: SEQ ID NO: 1:

```
GATCAAAACT GATGCAAATG GAGTAATTAA GGCAAATCAT CTAAAACCAG GTAAATACAC      60

TTTTGTTGAA ACAGAGGCTC CAGCAGGTTA TCAATTAAGT CAAGAAACTA GAGCTTTTGA     120

AATTAAAGCA AGCGCAGAAA ACAAACCACA AGTTGTTAAT ACTGGAAAGT TCGTCAATAA     180

AAGACTTCCA ATTACACCTA AAAGCCAGA ATTACCTAAG ACAGGAGAAG AACGAAATAC      240

TTTCTTGCCT ATAGTTGGTG TTGGACTATT AATGGTGGGT GCTACTTTAT ATGTATTTTT     300

TAAAAGACGT AAAATGTAAA ATTATATAAA AACATGGCTT TAGCCATGTT TTTGATTTGG     360

GAAAAGTGGT AGTGACTTAA TACAAAAATA TTTTAGTTTG TAATACCTAA AAATAATACT     420

TCAGTTTGCA GTATTCCAAT AAGTAAAAAA GATTTGGCTA TATTAGAACC ACCCAAAAAA     480

ACTCAAAATC ATGTAAATAT TAAGCTTGGA TTGGCCCAAT AGAGAAAATT TTTTCTTTCA     540

TCATTATAGT TTGCAAAATG GTATTCCAAA TGTAGTCACA GTAAATAAAA CAATGAAAAA     600

GATGTTAAAT GAGTTAGAAA TTGAGCCAAT AATTACAAGT GAGGTGTTAG ATAAACTTGT     660

GATAGTGTAC TACTAAGTTA AGGTATCGAT AATAAAGTAG TGGCAAAGTT AATGGGCATA     720

AAGATACATC AATGCTAATA AAAATATAAT TAAAAGAATA TGATAAAATA ATAAAAAACC     780

TTGTATATCA ACGATACAAG GTTTTTTATC TATGCCGAGT GCAGGATTGT TTAGATAGTT     840

TTCAAAGTTA AATACAGGCT CTATAAAGCT CTCAAAGTGT TCACTATAGA AAAGCTCTTA     900

AAGTGAAAAA TAAAATGGGG CAAATTGGGG GCATTTCAAG TTAAGAGTAT TCAAATATGT     960

AACTAAAAAA AATTATTTTT TTGAATTAGT GTTTTTCTAT TTGCATATTT TTTCGAGATT    1020

TTCTGTTTTG ATTATTATAT AATTATATTT ATATTTATAG TTATAGTTAT TGAGTTAAGT    1080
```

| TAGTGGGAGA TACA | ATG | AAA | TTA | TAT | ATA | GTT | GGT | AAT | GGC | TTT | GAT | TTA | 1130 |
|---|---|---|---|---|---|---|---|---|---|---|---|---|---|
| | Met | Lys | Leu | Tyr | Ile | Val | Gly | Asn | Gly | Phe | Asp | Leu | |
| | 1 | | | 5 | | | | | 10 | | | | |

| TCA | CAC | AAT | CTG | AAA | ACA | TCA | TAT | ACA | GAG | TTT | AGA | TTA | TAT | TTA | TTG | 1178 |
|---|---|---|---|---|---|---|---|---|---|---|---|---|---|---|---|---|
| Ser | His | Asn | Leu | Lys | Thr | Ser | Tyr | Thr | Glu | Phe | Arg | Leu | Tyr | Leu | Leu | |
| | 15 | | | | 20 | | | | | 25 | | | | | | |

| GAA | CAT | AGG | GAT | GAA | GTA | TAT | ACA | GAT | GAA | GAT | TTA | ATA | ATA | TCA | AAA | 1226 |
|---|---|---|---|---|---|---|---|---|---|---|---|---|---|---|---|---|
| Glu | His | Arg | Asp | Glu | Val | Tyr | Thr | Asp | Glu | Asp | Leu | Ile | Ile | Ser | Lys | |
| | 30 | | | | 35 | | | | | 40 | | | | | | |

| GGA | GAT | ATT | TTA | CGA | AAT | TTT | GAA | AGA | TAT | TGT | CAA | CCA | AAT | GAT | TTA | 1274 |
|---|---|---|---|---|---|---|---|---|---|---|---|---|---|---|---|---|
| Gly | Asp | Ile | Leu | Arg | Asn | Phe | Glu | Arg | Tyr | Cys | Gln | Pro | Asn | Asp | Leu | |
| 45 | | | | 50 | | | | | 55 | | | | | | 60 | |

| TGG | AGC | GAT | TTT | GAA | GAA | CAG | ACT | GAG | AAA | ATA | ATA | TCA | GAA | ATA | TCA | 1322 |
|---|---|---|---|---|---|---|---|---|---|---|---|---|---|---|---|---|
| Trp | Ser | Asp | Phe | Glu | Glu | Gln | Thr | Glu | Lys | Ile | Ile | Ser | Glu | Ile | Ser | |
| | | | 65 | | | | | 70 | | | | | 75 | | | |

| GAG | GGG | AAA | ATT | ATA | ATC | TTT | GAA | GAA | GAA | TGG | AGC | TGC | AAA | TTA | GAT | 1370 |
|---|---|---|---|---|---|---|---|---|---|---|---|---|---|---|---|---|
| Glu | Gly | Lys | Ile | Ile | Ile | Phe | Glu | Glu | Glu | Trp | Ser | Cys | Lys | Leu | Asp | |
| | | 80 | | | | | 85 | | | | | 90 | | | | |

| ATT | GGA | GGT | GAG | AGG | CAT | AAA | TTT | ATT | GAT | TGT | TTT | AAA | AAG | TTA | ATA | 1418 |
|---|---|---|---|---|---|---|---|---|---|---|---|---|---|---|---|---|
| Ile | Gly | Gly | Glu | Arg | His | Lys | Phe | Ile | Asp | Cys | Phe | Lys | Lys | Leu | Ile | |
| | 95 | | | | | 100 | | | | | 105 | | | | | |

| AAA | AAA | CAA | GAT | AGT | ACA | TTC | GAT | ACT | GAT | ATA | TAT | CAT | AAT | GAA | ATT | 1466 |
|---|---|---|---|---|---|---|---|---|---|---|---|---|---|---|---|---|
| Lys | Lys | Gln | Asp | Ser | Thr | Phe | Asp | Thr | Asp | Ile | Tyr | His | Asn | Glu | Ile | |
| 110 | | | | | 115 | | | | | 120 | | | | | | |

-continued

| | | |
|---|---|---|
| CAA GAG TAT GCC TTA AAG TAT TTT AAC AAT AAG GTA AGG GAA CTA TAT<br>Gln Glu Tyr Ala Leu Lys Tyr Phe Asn Asn Lys Val Arg Glu Leu Tyr<br>125                    130                    135                    140 | 1514 |
| ATA TGG GTT CCA TAT TTA TAT ATT AGT TTT CAA GAA TGG ATA CAA ACG<br>Ile Trp Val Pro Tyr Leu Tyr Ile Ser Phe Gln Glu Trp Ile Gln Thr<br>                    145                    150                    155 | 1562 |
| ATT ATT TTA AAA AAT ACG AAA AAT ATC TAT GAA ATA GAT GAA GAT TCG<br>Ile Ile Leu Lys Asn Thr Lys Asn Ile Tyr Glu Ile Asp Glu Asp Ser<br>              160                    165                    170 | 1610 |
| TCT GTA ATT TCC TTT AAC TAT ACA AAT ACT ATG GAA GAT GTT TAT CAA<br>Ser Val Ile Ser Phe Asn Tyr Thr Asn Thr Met Glu Asp Val Tyr Gln<br>          175                    180                    185 | 1658 |
| CAA AAA GAT GTA CTA CAT TTA CAT GGT TCT GTA AAA AAT CTA GAA GAT<br>Gln Lys Asp Val Leu His Leu His Gly Ser Val Lys Asn Leu Glu Asp<br>190                    195                    200 | 1706 |
| GTA GTA TTA GGA TTT CAT TCG CCA GAA ATA GAC GAC AAA TTA CCA GGG<br>Val Val Leu Gly Phe His Ser Pro Glu Ile Asp Asp Lys Leu Pro Gly<br>205                    210                    215                    220 | 1754 |
| TTA GAA ACA AGT TTT ACG AAG GAA TTT AAG GAA ACA CAA AGA ATG TTT<br>Leu Glu Thr Ser Phe Thr Lys Glu Phe Lys Glu Thr Gln Arg Met Phe<br>                    225                    230                    235 | 1802 |
| GCA GAA CAG GGT TCT AGA AAG CTT AAT TCT AAT AAG TTT TAT GAT GAA<br>Ala Glu Gln Gly Ser Arg Lys Leu Asn Ser Asn Lys Phe Tyr Asp Glu<br>              240                    245                    250 | 1850 |
| AAT ATA GGA AGA TTT TAT AAA CCA GTA AAT CTT TTA AAA GAC TCA ATT<br>Asn Ile Gly Arg Phe Tyr Lys Pro Val Asn Leu Leu Lys Asp Ser Ile<br>          255                    260                    265 | 1898 |
| GAG TCT TTT GTT AAA AAT AAA AAT ATT CAT GAA GTA ATA ATC TTA GGT<br>Glu Ser Phe Val Lys Asn Lys Asn Ile His Glu Val Ile Ile Leu Gly<br>270                    275                    280 | 1946 |
| CAT TCA TAT AAT AAG ATA GAC TGG GTT TAT TTT AAA GAA CTA GTC AGA<br>His Ser Tyr Asn Lys Ile Asp Trp Val Tyr Phe Lys Glu Leu Val Arg<br>285                    290                    295                    300 | 1994 |
| TGC GCC CCT GAA GCA AAA TAT TTA TTT AGC TAT TAT TCC CAA AAT GAT<br>Cys Ala Pro Glu Ala Lys Tyr Leu Phe Ser Tyr Tyr Ser Gln Asn Asp<br>                    305                    310                    315 | 2042 |
| AAA GAA AAC ATA AAT AAA ATT ATA TTG GAG AAT AAA TTT GAT ATT GAT<br>Lys Glu Asn Ile Asn Lys Ile Ile Leu Glu Asn Lys Phe Asp Ile Asp<br>              320                    325                    330 | 2090 |
| TGC GAA AAA ATA CAT GTA GAT AAC TTT AAA ATT AAA AAA GAT<br>Cys Glu Lys Ile His Val Asp Asn Phe Lys Ile Lys Lys Asp<br>          335                    340                    345 | 2132 |
| TAGCAAAAAT TTAGGAGTTT TATATGATTA TATTTATAGA CCCGAATTGC TAGTTGATTA | 2192 |
| TTTAGCCATG ACTTGATACC CGATAGAATA TCTTAAAGTC TCTGGTTCCA GTGATTAGC | 2252 |
| TGATTTTAAC AGTAAAGAAT ACGCTAAAAG TATCATCTCT AATTTCAATT GAAAACCTTG | 2312 |
| AGGCGAACGA CTTTTACAAC GCTCAGCTCC TAGATTTGTC AAAAAAGAGA AAACTCGCTC | 2372 |
| AATCACTTTT CTACGTTTTG AAAAATTAGG GAAAAGGATT TTCTTTCGCT TCATGTTCTT | 2432 |
| CCTGACAGGT GTCATTAGAT CAATTCCTTT TAATTCCAGC CTATCATGCA GTGACTGACC | 2492 |
| TAAATATCCC ATATCTCCAA GGACTGTTGG TGTCCCAAAT TGACTCAACA CTTCCTCGGC | 2552 |
| CATTGTACTG TCAGCTATTG AAGCAGGAGT AATTGTGTAG TCTATGACAT AGCCTGATTC | 2612 |
| ACTGACTAAA GCATGACATT TACATCCATA GAAGTACTGT CCCTTTGTAA CATTGTAGCC | 2672 |
| AACATTTGCA TAATCTCCAA GAACTTTGCT TCTGAAATTA CGAATCGACT GACACAAAGG | 2732 |
| AATGGGGAAG CTGTCAATAA TGGATACACT CATTCCTTCA ACCTCTTTAA AGACGAGTGC | 2792 |
| TTGGCGAATG ACTTGGATAC TCGGTAAGAG GGCATTACAA CGGCGGACAA AGCGAGAATA | 2852 |

```
TTCTAGGAAA TTAGGAAATA AACTTTGAGC CAATTGGTGC TTAGCTTTAA GTGTTTCACT       2912

AAAATGCAGT ACGCCCCATA GGTAACAAGC GATAACTAAG CAATCTGATG TTGCGAGATG       2972

GACGTTCTTT CGGTTTTGAA CCTCAAGGGG ACACTCGTTT GATAAATCGT CTCAATGGTT       3032

GTCAGTAAAT AAACCAAAAA CTTTTGGAAG TGTGCTATTA TAAGTCATAT AAGTCGTGCG       3092

CTTTCTAATG CTTAGTGGGT TAAGATTAGG ATAGCACGAC TTATTTATTT TCCAATGAAA       3152

TTAACTAGCA ATTCGGGTTT TCTTAATTTT TTTTATAAAA AAATTACTCC TAAAGCAGAG       3212

TAATTTTATT GTTAATTTTT ATCAGAGATT ATTCCAAAAA TTTTTCTGAT AAAAATGAAG       3272

TATCACTCCT ACCGAAAATC CTAAAAGGAG GACTAGGGCA AGGTTAACAA CTAAAGGATA       3332

TGGAATAAAG ATAATCAGGG CAATAATTGC TCCAATGAGT GCTCCTGCTC CCAAAAGCGT       3392

AGCAAAGAAA ATGATAAAAA CCCGAAATCC CCCAGAACCT CTTGTAAAAA GTTGAGTCAA       3452

CGCAGTCCAA TTTAAATTTA AGAGATGCCA ATCTCTGACA AAATAATGAA GTGAAATCAG       3512

ATATACCCCA ATAACATTCC CAATTAACAG CCCAAGAGC  AAGGTAACAG GGACTTTCAG       3572

TAAAATACCA ATCACTAAAG ATAAGATTAA GTCAAGAACT AGTTGAATAA AAAAGGCAAA       3632

ATGAAATTTC ACTCTGAGAT AGAAATTCAA CTTCATGGGT AAGCTTTTAA AATAATTAAA       3692

ATTTTCCCGA TC                                                          3704
```

(2) INFORMATION FOR SEQ ID NO: 2:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Leu Tyr Ile Val Gly Asn Gly Phe Asp Leu Ser His Asn Leu
  1               5                  10                  15

Lys Thr Ser Tyr Thr Glu Phe Arg Leu Tyr Leu Glu His Arg Asp
             20                  25                  30

Glu Val Tyr Thr Asp Glu Asp Leu Ile Ile Ser Lys Gly Asp Ile Leu
             35                  40                  45

Arg Asn Phe Glu Arg Tyr Cys Gln Pro Asn Asp Leu Trp Ser Asp Phe
 50                  55                  60

Glu Glu Gln Thr Glu Lys Ile Ile Ser Glu Ile Ser Glu Gly Lys Ile
 65                  70                  75                  80

Ile Ile Phe Glu Glu Glu Trp Ser Cys Lys Leu Asp Ile Gly Glu
                 85                  90                  95

Arg His Lys Phe Ile Asp Cys Phe Lys Lys Leu Ile Lys Gln Asp
                100                 105                 110

Ser Thr Phe Asp Thr Asp Ile Tyr His Asn Glu Ile Gln Glu Tyr Ala
             115                 120                 125

Leu Lys Tyr Phe Asn Asn Lys Val Arg Glu Leu Tyr Ile Trp Val Pro
 130                 135                 140

Tyr Leu Tyr Ile Ser Phe Gln Glu Trp Ile Gln Thr Ile Leu Lys
145                 150                 155                 160

Asn Thr Lys Asn Ile Tyr Glu Ile Asp Glu Asp Ser Ser Val Ile Ser
                 165                 170                 175

Phe Asn Tyr Thr Asn Thr Met Glu Asp Val Tyr Gln Gln Lys Asp Val
             180                 185                 190

Leu His Leu His Gly Ser Val Lys Asn Leu Glu Asp Val Val Leu Gly
             195                 200                 205
```

```
Phe His Ser Pro Glu Ile Asp Asp Lys Leu Pro Gly Leu Glu Thr Ser
    210                 215                 220

Phe Thr Lys Glu Phe Lys Glu Thr Gln Arg Met Phe Ala Glu Gln Gly
225                 230                 235                 240

Ser Arg Lys Leu Asn Ser Asn Lys Phe Tyr Asp Glu Asn Ile Gly Arg
                245                 250                 255

Phe Tyr Lys Pro Val Asn Leu Leu Lys Asp Ser Ile Glu Ser Phe Val
            260                 265                 270

Lys Asn Lys Asn Ile His Glu Val Ile Ile Leu Gly His Ser Tyr Asn
        275                 280                 285

Lys Ile Asp Trp Val Tyr Phe Lys Glu Leu Val Arg Cys Ala Pro Glu
    290                 295                 300

Ala Lys Tyr Leu Phe Ser Tyr Tyr Ser Gln Asn Asp Lys Glu Asn Ile
305                 310                 315                 320

Asn Lys Ile Ile Leu Glu Asn Lys Phe Asp Ile Asp Cys Glu Lys Ile
                325                 330                 335

His Val Asp Asn Phe Lys Ile Lys Lys Asp
            340                 345

(2) INFORMATION FOR SEQ ID NO: 3:

(i) SEQUENCE CHARACTERISTICS:
        (A) LENGTH: 1345 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Lactococcus lactis (ix) FEATURE:
         (A) NAME/KEY: CDS
         (B) LOCATION:246..1283

(xi) SEQUENCE DESCRIPTION: SEQ ID NO: 3:

AAATACAGGC TCTATAAAGC TCTCAAAGTG TTCACTATAG AAAAGCTCTT AAAGTGAAAA      60

ATAAAATGGG GCAAATTGGG GGCATTTCAA GTTAAGAGTA TTCAAATATG TAACTAAAAA     120

AAATTATTTT TTTGAATTAG TGTTTTTCTA TTTGCATATT TTTTCGAGAT TTTCTGTTTT    180

GATTATTATA TAATTATATT TATATTTATA GTTATAGTTA TTGAGTTAAG TTAGTGGGAG    240

ATACA ATG AAA TTA TAT ATA GTT GGT AAT GGC TTT GAT TTA TCA CAC        287
      Met Lys Leu Tyr Ile Val Gly Asn Gly Phe Asp Leu Ser His
        1               5                  10

AAT CTG AAA ACA TCA TAT ACA GAG TTT AGA TTA TAT TTA TTG GAA CAT      335
Asn Leu Lys Thr Ser Tyr Thr Glu Phe Arg Leu Tyr Leu Leu Glu His
 15              20                  25                  30

AGG GAT GAA GTA TAT ACA GAT GAA GAT TTA ATA ATA TCA AAA GGA GAT      383
Arg Asp Glu Val Tyr Thr Asp Glu Asp Leu Ile Ile Ser Lys Gly Asp
                 35                  40                  45

ATT TTA CGA AAT TTT GAA AGA TAT TGT CAA CCA AAT GAT TTA TGG AGC      431
Ile Leu Arg Asn Phe Glu Arg Tyr Cys Gln Pro Asn Asp Leu Trp Ser
             50                  55                  60

GAT TTT GAA GAA CAG ACT GAG AAA ATA ATA TCA GAA ATA TCA GAG GGG      479
Asp Phe Glu Glu Gln Thr Glu Lys Ile Ile Ser Glu Ile Ser Glu Gly
 65                  70                  75
```

-continued

```
AAA ATT ATA ATC TTT GAA GAA GAA TGG AGC TGC AAA TTA GAT ATT GGA    527
Lys Ile Ile Ile Phe Glu Glu Glu Trp Ser Cys Lys Leu Asp Ile Gly
 80                  85                  90

GGT GAG AGG CAT AAA TTT ATT GAT TGT TTT AAA AAG TTA ATA AAA AAA    575
Gly Glu Arg His Lys Phe Ile Asp Cys Phe Lys Lys Leu Ile Lys Lys
 95                 100                 105                 110

CAA GAT AGT ACA TTC GAT ACT GAT ATA TAT CAT AAT GAA ATT CAA GAG    623
Gln Asp Ser Thr Phe Asp Thr Asp Ile Tyr His Asn Glu Ile Gln Glu
                115                 120                 125

TAT GCC TTA AAG TAT TTT AAC AAT AAG GTA AGG GAA CTA TAT ATA TGG    671
Tyr Ala Leu Lys Tyr Phe Asn Asn Lys Val Arg Glu Leu Tyr Ile Trp
            130                 135                 140

GTT CCA TAT TTA TAT ATT AGT TTT CAA GAA TGG ATA CAA ACG ATT ATT    719
Val Pro Tyr Leu Tyr Ile Ser Phe Gln Glu Trp Ile Gln Thr Ile Ile
        145                 150                 155

TTA AAA AAT ACG AAA AAT ATC TAT GAA ATA GAT GAA GAT TCG TCT GTA    767
Leu Lys Asn Thr Lys Asn Ile Tyr Glu Ile Asp Glu Asp Ser Ser Val
160                 165                 170

ATT TCC TTT AAC TAT ACA AAT ACT ATG GAA GAT GTT TAT CAA CAA AAA    815
Ile Ser Phe Asn Tyr Thr Asn Thr Met Glu Asp Val Tyr Gln Gln Lys
175                 180                 185                 190

GAT GTA CTA CAT TTA CAT GGT TCT GTA AAA AAT CTA GAA GAT GTA GTA    863
Asp Val Leu His Leu His Gly Ser Val Lys Asn Leu Glu Asp Val Val
                195                 200                 205

TTA GGA TTT CAT TCG CCA GAA ATA GAC GAC AAA TTA CCA GGG TTA GAA    911
Leu Gly Phe His Ser Pro Glu Ile Asp Asp Lys Leu Pro Gly Leu Glu
            210                 215                 220

ACA AGT TTT ACG AAG GAA TTT AAG GAA ACA CAA AGA ATG TTT GCA GAA    959
Thr Ser Phe Thr Lys Glu Phe Lys Glu Thr Gln Arg Met Phe Ala Glu
        225                 230                 235

CAG GGT TCT AGA AAG CTT AAT TCT AAT AAG TTT TAT GAT GAA AAT ATA   1007
Gln Gly Ser Arg Lys Leu Asn Ser Asn Lys Phe Tyr Asp Glu Asn Ile
240                 245                 250

GGA AGA TTT TAT AAA CCA GTA AAT CTT TTA AAA GAC TCA ATT GAG TCT   1055
Gly Arg Phe Tyr Lys Pro Val Asn Leu Leu Lys Asp Ser Ile Glu Ser
255                 260                 265                 270

TTT GTT AAA AAT AAA AAT ATT CAT GAA GTA ATA ATC TTA GGT CAT TCA   1103
Phe Val Lys Asn Lys Asn Ile His Glu Val Ile Ile Leu Gly His Ser
                275                 280                 285

TAT AAT AAG ATA GAC TGG GTT TAT TTT AAA GAA CTA GTC AGA TGC GCC   1151
Tyr Asn Lys Ile Asp Trp Val Tyr Phe Lys Glu Leu Val Arg Cys Ala
            290                 295                 300

CCT GAA GCA AAA TAT TTA TTT AGC TAT TAT TCC CAA AAT GAT AAA GAA   1199
Pro Glu Ala Lys Tyr Leu Phe Ser Tyr Tyr Ser Gln Asn Asp Lys Glu
        305                 310                 315

AAC ATA AAT AAA ATT ATA TTG GAG AAT AAA TTT GAT ATT GAT TGC GAA   1247
Asn Ile Asn Lys Ile Ile Leu Glu Asn Lys Phe Asp Ile Asp Cys Glu
320                 325                 330

AAA ATA CAT GTA GAT AAC TTT AAA ATT AAA AAA GAT TAGCAAAAAT        1293
Lys Ile His Val Asp Asn Phe Lys Ile Lys Lys Asp
335                 340                 345

TTAGGAGTTT TATATGATTA TATTTATAGA CCCGAATTGC TAGTTGATTA TT         1345
```

(2) INFORMATION FOR SEQ ID NO: 4:

(i) SEQUENCE CHARACTERISTICS:
        (A) LENGTH: 346 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Leu Tyr Ile Val Gly Asn Gly Phe Asp Leu Ser His Asn Leu
 1               5                  10                  15
Lys Thr Ser Tyr Thr Glu Phe Arg Leu Tyr Leu Glu His Arg Asp
             20                  25                  30
Glu Val Tyr Thr Asp Glu Asp Leu Ile Ile Ser Lys Gly Asp Ile Leu
             35                  40                  45
Arg Asn Phe Glu Arg Tyr Cys Gln Pro Asn Asp Leu Trp Ser Asp Phe
         50                  55                  60
Glu Glu Gln Thr Glu Lys Ile Ile Ser Glu Ile Ser Glu Gly Lys Ile
 65                  70                  75                  80
Ile Ile Phe Glu Glu Glu Trp Ser Cys Lys Leu Asp Ile Gly Gly Glu
                 85                  90                  95
Arg His Lys Phe Ile Asp Cys Phe Lys Lys Leu Ile Lys Lys Gln Asp
                100                 105                 110
Ser Thr Phe Asp Thr Asp Ile Tyr His Asn Glu Ile Gln Glu Tyr Ala
             115                 120                 125
Leu Lys Tyr Phe Asn Asn Lys Val Arg Glu Leu Tyr Ile Trp Val Pro
    130                 135                 140
Tyr Leu Tyr Ile Ser Phe Gln Glu Trp Ile Gln Thr Ile Ile Leu Lys
145                 150                 155                 160
Asn Thr Lys Asn Ile Tyr Glu Ile Asp Glu Asp Ser Ser Val Ile Ser
                165                 170                 175
Phe Asn Tyr Thr Asn Thr Met Glu Asp Val Tyr Gln Gln Lys Asp Val
            180                 185                 190
Leu His Leu His Gly Ser Val Lys Asn Leu Glu Asp Val Val Leu Gly
    195                 200                 205
Phe His Ser Pro Glu Ile Asp Asp Lys Leu Pro Gly Leu Glu Thr Ser
210                 215                 220
Phe Thr Lys Glu Phe Lys Glu Thr Gln Arg Met Phe Ala Glu Gln Gly
225                 230                 235                 240
Ser Arg Lys Leu Asn Ser Asn Lys Phe Tyr Asp Glu Asn Ile Gly Arg
                245                 250                 255
Phe Tyr Lys Pro Val Asn Leu Leu Lys Asp Ser Ile Glu Ser Phe Val
            260                 265                 270
Lys Asn Lys Asn Ile His Glu Val Ile Ile Leu Gly His Ser Tyr Asn
    275                 280                 285
Lys Ile Asp Trp Val Tyr Phe Lys Glu Leu Val Arg Cys Ala Pro Glu
    290                 295                 300
Ala Lys Tyr Leu Phe Ser Tyr Tyr Ser Gln Asn Asp Lys Glu Asn Ile
305                 310                 315                 320
Asn Lys Ile Ile Leu Glu Asn Lys Phe Asp Ile Asp Cys Glu Lys Ile
                325                 330                 335
His Val Asp Asn Phe Lys Ile Lys Lys Asp
                340                 345
```

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: misc_signal
            (B) LOCATION:6..11
            (D) OTHER INFORMATION:/function= "BamHI restriction site"

(ix) FEATURE:
            (A) NAME/KEY: misc_structure
            (B) LOCATION:12..31
            (D) OTHER INFORMATION:/function= "sequence homologous to
                the cDNA corresponding to nucleotides 1326-1345
                of SEQ ID NO: 3"

(xi) SEQUENCE DESCRIPTION: SEQ ID NO: 5:

TCATAGGATC CAATAATCAA CTAGCAATTC G                                31

(2) INFORMATION FOR SEQ ID NO: 6:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: misc_signal
            (B) LOCATION:6..11
            (D) OTHER INFORMATION:/function= "SalI restriction site"

(ix) FEATURE:
            (A) NAME/KEY: misc_structure
            (B) LOCATION:12..31
            (D) OTHER INFORMATION:/function= "sequence homologous to
                to nucleotides 1-20 of SEQ ID NO:3"

(xi) SEQUENCE DESCRIPTION: SEQ ID NO: 6:

CATTAGTCGA CAAATACAGG CTCTATAAAG C                                31

(2) INFORMATION FOR SEQ ID NO: 7:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (ix) FEATURE:
            (A) NAME/KEY: misc_signal
            (B) LOCATION:6..11
            (D) OTHER INFORMATION:/function= "BamHI restriction site"

(xi) SEQUENCE DESCRIPTION: SEQ ID NO: 7:

TCATAGGATC CTTAACAATA AAATTACTCT GC                               32

(2) INFORMATION FOR SEQ ID NO: 8:

(i) SEQUENCE CHARACTERISTICS:
            (A) LENGTH: 32 base pairs
            (B) TYPE: nucleic acid
            (C) STRANDEDNESS: single -continued

```
    (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: misc_signal
    (B) LOCATION:6..11
    (D) OTHER INFORMATION:/function= "SalI restriction site"

(xi) SEQUENCE DESCRIPTION: SEQ ID NO: 8:

CATTAGTCGA CTTAAATTTG ATATTGATTG CG                                            32
```